(12) United States Patent
Larsen et al.

(10) Patent No.: US 8,792,950 B2
(45) Date of Patent: Jul. 29, 2014

(54) OXIMETRY WITH REMOTE DISPLAY

(75) Inventors: Christopher Larsen, Rockford, MN (US); Timothy L. Johnson, Plymouth, MN (US); Scott Everett Blomberg, Plymouth, MN (US); Charles U. Smith, Minnetonka, MN (US); Jayant Parthasarathy, Eden Prairie, MN (US)

(73) Assignee: Nonin Medical, Inc., Plymouth, MN (US)

( * ) Notice: Subject to any disclaimer, the term of this patent is extended or adjusted under 35 U.S.C. 154(b) by 707 days.

(21) Appl. No.: 12/794,097

(22) Filed: Jun. 4, 2010

(65) Prior Publication Data

US 2010/0312079 A1   Dec. 9, 2010

Related U.S. Application Data

(60) Provisional application No. 61/184,522, filed on Jun. 5, 2009.

(51) Int. Cl.
*A61B 5/00* (2006.01)

(52) U.S. Cl.
USPC ........................................................ 600/323

(58) Field of Classification Search
USPC ........................................................ 600/323
See application file for complete search history.

(56) References Cited

U.S. PATENT DOCUMENTS 6,141,572 A * 10/2000 Haas .............................. 600/331
6,416,471 B1    7/2002 Kumar et al.
2004/0102687 A1    5/2004 Brashears et al.
2006/0094943 A1 *  5/2006 Van Slyke ...................... 600/323
2006/0281983 A1 * 12/2006 Al-Ali et al. ................... 600/323
2008/0281168 A1   11/2008 Gibson et al.
2008/0287752 A1 * 11/2008 Stroetz et al. ................. 600/301

FOREIGN PATENT DOCUMENTS

WO   WO-2010141838 A1   12/2010

OTHER PUBLICATIONS

International Application Serial No. PCT/US2010/037431, Search Report mailed Aug. 18, 2010, 5 pgs.
International Application Serial No. PCT/US2010/037431, Written Opinion mailed Aug. 18, 2010, 6 pgs.
European Application Serial No. 10722276.2, Office Action mailed Jan. 18, 2012, 2 pgs.
International Application Serial No. PCT/US2010/037431, International Preliminary Report on Patentability Mailed Dec. 15, 2011, 7 pgs.

* cited by examiner

*Primary Examiner* — Clayton E Laballe
*Assistant Examiner* — Dennis Hancock
(74) *Attorney, Agent, or Firm* — Schwegman, Lundberg & Woessner, P.A.

(57) ABSTRACT

A device includes a first sensor coupler that is configured to receive a first input signal from a first sensor. The first input signal corresponds to a first physiological parameter and is based on optical excitation of a tissue. The device includes a processor coupled to the first sensor coupler. The processor is configured to generate an output signal based on the first input signal. The first physiological parameter is encoded in the output signal. The output signal differs from the first input signal. The device includes an output coupler configured to communicate the output signal to a remote device.

21 Claims, 3 Drawing Sheets

OXIMETRY WITH REMOTE DISPLAY

CLAIM OF PRIORITY

This document claims the benefit of priority, under 35 U.S.C. Section 119(e), to Chris Larsen et al., U.S. Provisional Patent Application Ser. No. 61/184,522, entitled "OXIMETRY WITH REMOTE DISPLAY," filed on Jun. 5, 2009, which is incorporated herein by reference.

BACKGROUND

Technology for measuring oximetry is inadequate. Oximetry can be determined based on optical properties of tissue. However, systems for analyzing those properties do not provide satisfactory results.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A plurality of oximeter sensors can be coupled to a module. The module can be configured to coordinate or synchronize excitation and detection of optical signals for the coupled sensors. The module can also include a processor configured to implement an algorithm to generate data corresponding to the signals received from the sensors. The module can include memory for storing calibration data, identification data, and coefficients used in generating data. The module can be coupled to a remote device. The remote device can include, or be coupled to, a display, a printer, a storage device, or a network.

In one example, the sensor includes a memory. The sensor memory can be used to store calibration data, identification data, coefficients, or other data for use in providing information to the module.

Figure 1:
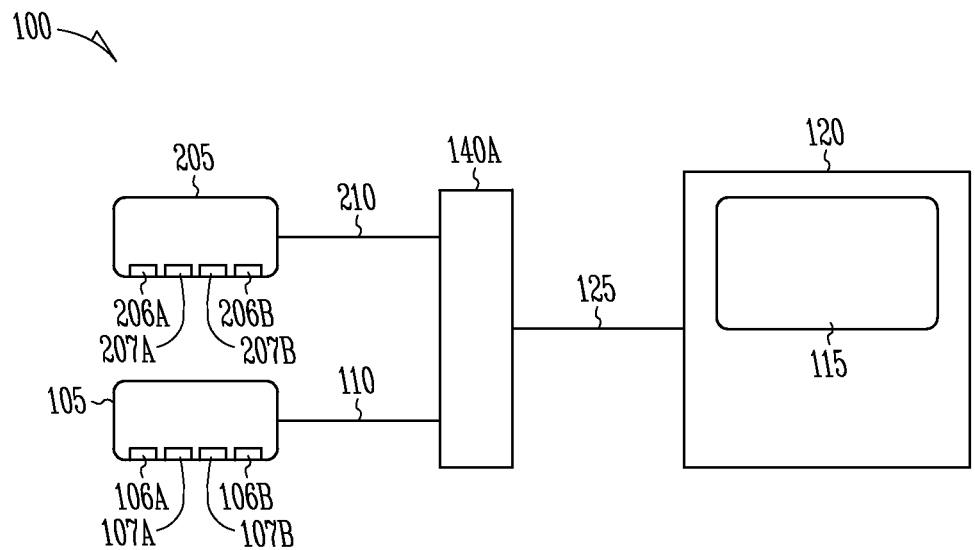
FIG. 1 illustrates a block diagram of an oximetry system according to one example.

FIG. 1 illustrates a block diagram of oximetry system 100 according to one example. System 100 includes sensor 105, sensor 205, module 140A and remote device 120.

In the example illustrated, sensor 105 and sensor 205 are configured for optical detection of one or more tissue parameters. However, in other examples, sensor 105 and sensor 205 can be configured for measuring a parameter using non-optical means such as, for example, thermal, pressure, and other detection means.

Sensor 105 includes optical detector 107A and optical detector 107B. Detectors 107A and 107B can include a photodetector responsive to light of a particular wavelength. Sensor 105 also includes emitter 106A and emitter 106B. The arrangement of emitters and detectors can be configured to provide a selected depth of penetration within tissue and tailored for use at a particular wavelength of sensitivity. Sensor 205 also includes detector 207A, emitter 206A, emitter 206B, and detector 207B.

A sensor can include a combination of any number of detectors and any number of emitters. An emitter can be configured to emit light having any number of wavelengths, such as two, three, or four different wavelengths.

In the example shown, sensors 105 and 205 are configured to be positioned on different sites of a patient or tissue.

Sensor 105 is coupled to module 140A by link 110 and sensor 205 is coupled to module 140A by link 210. Any of link 110 and link 210 can include a wired connection or a wireless coupling. In one example, either of link 110 and link 210 includes a wired connection of approximately 18" length. In one example, either of link 110 and link 210 can include a fiber optic element or a radio frequency communication link.

Module 140A is coupled to remote device 120 by link 125. Link 125 can include a wired or wireless communication channel. For example, link 125 can include an electrically wired line of approximately 12' length or include a radio frequency or infrared communication link.

In the example shown, remote device 120 includes screen 115 which can include a display screen or a touch screen suitable for both displaying data and receiving manual input.

Remote device 120 can include an application-specific device. For example, a particular module can be configured to generate fully-processed data from a sensor and communicate that data at a signal level that is substantially immune from an external noise source. The data communicated between the module and the remote device, according to one example, is digitized and encoded with oximetry values. As such, a remote device can be configured to receive, display, or store the oximetry values, without need of further processing. The module can provide a digital signal that is fully processed and encoded with a calculated value for regional oximetry or other physiological parameter. The remote device can display the received information and render a visible depiction of the data without need for further processing (such as calibration or amplification).

Figure 2:
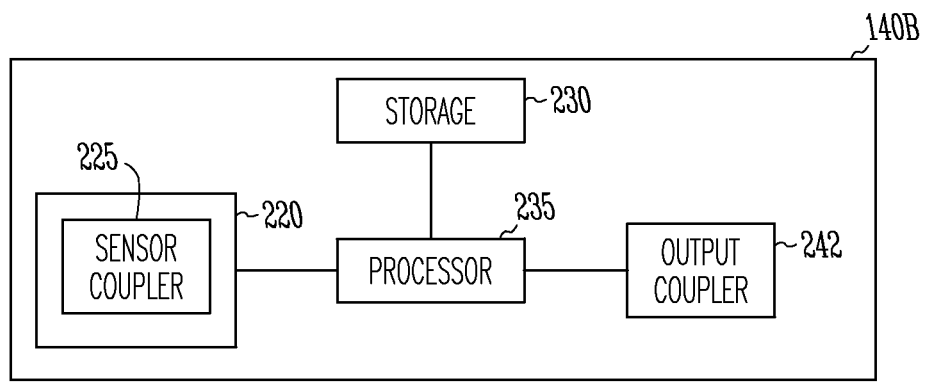
FIG. 2 illustrates a block diagram of a portion of an oximetry system according to one example.

FIG. 2 illustrates block a diagram of module 140B for an oximetry system according to one example. Module 140B, which compares with module 140A, includes input unit 220 (having sensor coupler 225), storage 230, processor 235, and output coupler 242. Module 140B can include a housing to which some or all other components are affixed.

In the example shown, input unit 220 includes one sensor coupler, however more than one sensor coupler is also contemplated. Sensor coupler 225 can include at least one of any of a radio frequency (RF) transceiver, an optical coupler, or an electrical connector. In one example, either input unit 220 or sensor coupler 225 is configured to discern identification information from a particular coupled sensor (such as sensor 105 or sensor 205). For example, if sensor coupler 225 includes an electrical connector, a feature of the connector can be engaged to register the identity of the connected sensor. A coupler, as used herein, can also include an electrical conductor or an optical link without a separate connector element.

Storage 230 can include one or more switches (such as a dual in-line package switch array), manual switches, or digital memory. Storage 230 can provide storage for calibration information, mathematical coefficients, data, and instructions for implementing an algorithm. A sensor (such as sensor 105 or sensor 205), processor 235, or other source (such as a manual input device) can provide the content held in storage 230.

Processor 235 can include an analog circuit or a digital circuit. In one example, processor 235 includes a digital processor configured to implement a method such as that described elsewhere in this document. In one example, processor 235 includes an analog-to-digital converter (ADC), an amplifier, a filter, a digital-to-analog converter (DAC), or other circuit. In one example, processor 235 is configured to generate, or monitor for, a timing signal. The timing signal can be used to synchronize communications and other functions as to the various elements of the system.

Output coupler 242 can include an RF transceiver, an optical coupler, or an electrical coupler. In one example, module 140B includes a rechargeable power supply and output coupler 242 includes circuitry to manage the rechargeable power supply.

Other elements of module 140B are also contemplated, including for example, a power supply, a recharging unit, a display, and a user-input device.

Figure 3:
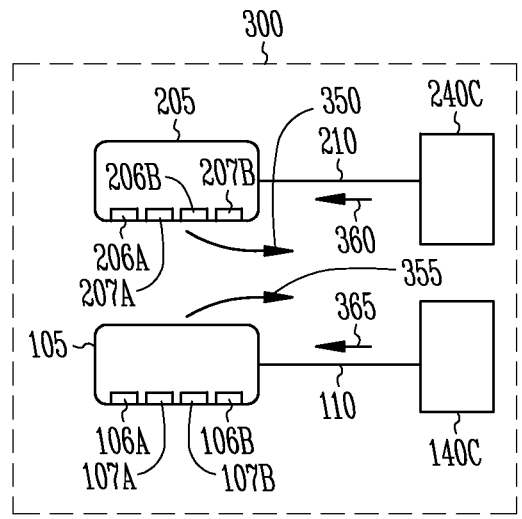
FIG. 3 illustrates a block diagram of a portion of an oximetry system according to one example.
Figure 4:
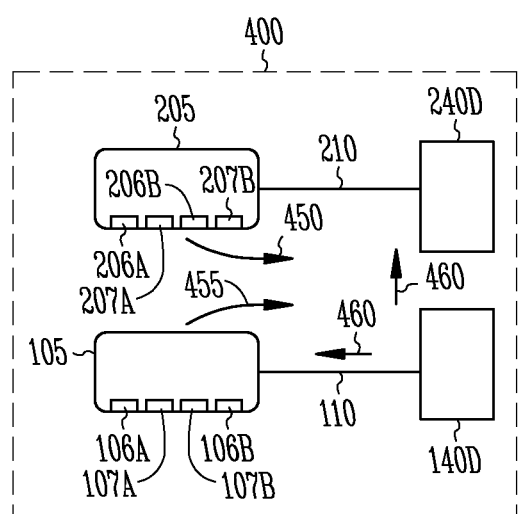
FIG. 4 illustrates a block diagram of a portion of an oximetry system according to one example.

FIGS. 3 and 4 illustrate examples including multiple modules, each of which is coupled to a sensor. In contrast to FIG. 1, in which a particular module is coupled to two sensors, the modules of FIGS. 3 and 4 are each coupled to a single sensor.

Timing as to the emission of light into tissue and as to detecting light by the sensors can be coordinated in a number of different manners. For example, a particular module can manage the timing as to one or multiple sensors coupled to that particular module. In one example, the sensors are configured to arbitrate the roles of master and slave and timing is managed independent of the module to which the various sensors are coupled. In one example, the module assigns roles to the various sensors.

In one example, the host (or display) device manages the timing as to multiple modules connected to the host. The timing can be synchronized by the host or by the modules themselves.

In one example, the sensors self-synchronize. In one example, the host provides synchronization for the sensors. In this case, the host sends a master synchronization signal and a junction cable connecting the oximeter modules to the display splits and adjusts that signal so that each module receives an individual timing signal. In one example, a module generates and provides a master synchronization signal to other connected modules through a junction cable.

Synchronization can refer to coordination of the light emission as to the various sensors, data detection as to the various sensors, data communications between modules, data communications between modules and remote device, or data communication between a sensor and a module.

As used herein, synchronization can refer to time-wise coordination of multiple sensors to reduce or eliminate interference arising from cross talk. For example, an emitter of a first sensor can produce an optical signal that can be detected by any of a plurality of detectors of a multiple sensor application. As such, in the absence of synchronization as to the multiple sensors, erroneous oxygenation data may be generated. Synchronization, in this context, serves to ensure that a particular detector is providing an output signal corresponding to a particular, selected emitter and not providing a signal corresponding to other emitters.

Synchronization can also refer to coordination of communications between multiple sensors coupled to a particular module or between multiple modules coupled to a particular host (or remote device). Synchronization can be in the time domain, frequency domain or based on other parameter.

As such, synchronization can refer to operation of a first module in a coordinated manner relative to operation of a second module. The first and second modules can be configured to coordinate in a master-slave relationship or in a peer-to-peer manner with the host providing a control signal to manage the modules. The modules can communicate with each other or communicate with the host via a wireless communication channel or a wired communication channel.

In addition, synchronization can refer to operation of a first sensor in a coordinated manner relative to operation of a second sensor. The first and second sensors can be configured to coordinate in a master-slave relationship or in a peer-to-peer manner with a module or a host providing a control signal to manage the sensors. The sensors can communicate with each other, communicate with a module, or communicate with the host via a wireless communication channel or a wired communication channel.

In one example, a remote device provides a synchronization signal to the particular modules. The synchronization signal represents a time-wise allocation during which each module is able to communicate when reporting data to the remote device. During the corresponding window of time, each module is able to send stored data or real-time data to the remote device.

In one example, a module is configured to independently manage synchronization relative to other modules in the system. As such, the module executes an algorithm to determine available times for exchanging data with the remote device. During those times, the module can communicate with the remote device and at other times, the module is precluded from communicating.

In a similar manner, a sensor can be configured to independently manage synchronization relative to other sensors in the system. As such, one sensor executes an algorithm to determine available times for exchanging data with the module. During those times, the sensor can communicate with the module and at other times, the sensor is precluded from communicating. The sensor, in this example, includes circuitry or a processor with executable instructions to determine available times.

In one example, a remote device includes a synchronization unit that provides synchronization information to a plurality of modules. The synchronization unit can be integrated with the remote device or the synchronization unit can be a stand-alone device that is in communication with a processor (such as a computer) by a communication channel (wired or wireless).

Synchronization (whether managed by a sensor, a module, a dedicated synchronization unit, or a remote device) ensures that one branch of a system does not interfere with operations of a second branch of a system. As such, the element providing synchronization serves as an arbiter in coordinating communications or other operations.

FIG. 3 illustrates a block diagram of portion 300 of an oximetry system according to one example. Portion 300 includes module 140C coupled to sensor 105 and module 240C coupled to sensor 205. In this example, modules 140C and 240C control the synchronization of the sensor functions. In particular, module 140C generates and delivers a periodic timing signal as shown by arrow 365 and module 240C generates and delivers a periodic timing signal as shown by arrow 360. In response to the various timing signals provided to the different sensors (here, sensors 105 and 205), the sensors perform certain functions in a manner configured to reduce interference as to the different elements. For example, in reply to the timing signals from modules 140C and 240C, sensor 205 and sensor 105 alternately emit light and detect light on selected optical pathways through the tissue. Sensor 205 provides synchronized data as denoted by the path corresponding to arrow 350 and sensor 105 provides synchronized data as denoted by the path corresponding to arrow 355. Module 140C and module 240C are coupled to a remote device (not shown in this figure) by a wired or wireless communication channel. An example of a wired communication channel includes a trunk cable.

FIG. 4 illustrates a block diagram of portion 400 of an oximetry system according to one example. Portion 400 includes modules 140D and 240D connected to sensor 105 and sensor 205, respectively. In this example, module 140D generates a master synchronization signal that is used to time the measurements and communication of module 140D and is also sent to module 240D to time that module's measurements and communication. For example, module 140D provides a timing signal as denoted by arrows 460. In the absence of a synchronization signal appearing at module 240D within a certain timeframe, module 240D determines that there are no other connected modules, and thus, module 240D generates the master signal itself and sends it to any other connected modules.

Figure 5:
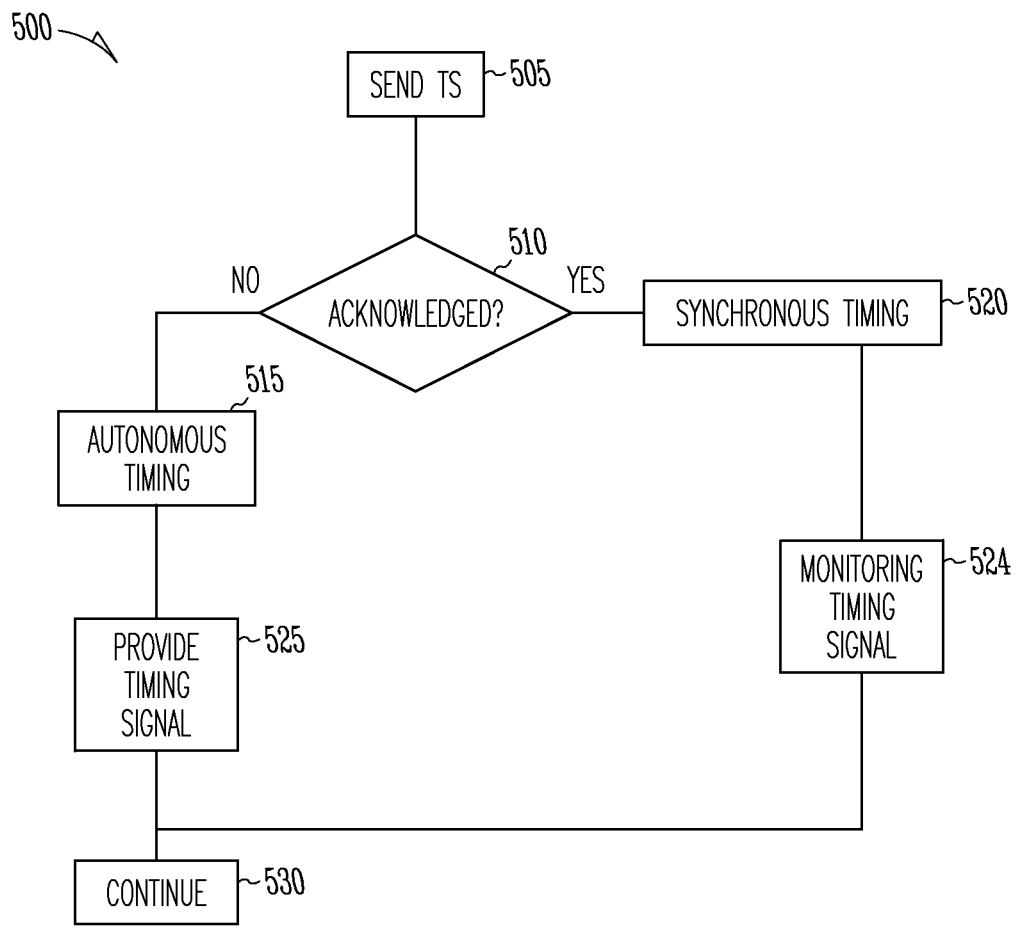
FIG. 5 illustrates a flow chart of a method according to one example.

FIG. 5 illustrates flow chart of method 500 according to one example. In the example shown, a timing signal is sent at 505 from, for example, module 140C. In the event, at 510, that module 240C does not receive a timing signal within a specific timeframe, then at 515, module 240C proceeds with autonomous timing. As such, module 240C provides a periodic timing signal to other modules in the same system as denoted by 525 and processing continues at 530. If module 240C receives a timing signal within a specified timeframe, it then enters a synchronous mode, as denoted at 520. During synchronous timing, module 240C continues to monitor for a timing signal (as denoted by 524). As such, all connected modules monitor for periodic timing signals generated by module 140C, 240C, or any other module acting as a master (as shown at 525) and continue to perform sensing functions as denoted by 530.

ADDITIONAL NOTES

The module can be coupled to one or more sensors by a wired or wireless connection. In one example, the module is coupled to a sensor by a wired connection having a length less than two meters. For example, an electrical conductor of approximately 18" can be used to couple one type of sensor to a module. In one example, the module is coupled to a sensor by an optical conductive element. In addition, the module can communicate with the remote device using a wired or wireless communication link. The link to the remote device can be of any length, such as 12 feet.

In one example, the sensor is configured to generate a signal based on a measured optical parameter. In one example, the sensor provides no signal processing and delivers a raw signal to the module. The module provides a timing signal to the sensor. The timing signal is used by the sensor to control excitation of a light emitter and detection of an optical signal by a detector. In one example, the timing signal provided by the module is a periodic pulse.

In one example, the module provides all oximetry analysis for use by the remote device and the remote device functions as a display device only. In one example, the module provides some oximetry analysis function. In this example, the remote device receives the partially-processed data and displays a result after further processing.

Any number of sensors can be coupled to a particular module. For example, one sensor can be coupled to a module.

In another example, two or more sensors are coupled to a particular module, such as that used for regional oximetry. The module can provide a timing signal to one sensor (or all sensors) and one sensor takes the role of master and all other sensors can function as slaves. In one example, the module allows the sensors to self-organize. As such, the module can be configured to monitor for a sensor-supplied timing signal and following acknowledgement, the sensors exchange timing information independent of the module.

In one example, if the module fails to receive a timing signal from a sensor, the module provides a timing signal on which a sensor can synchronize.

Any number of modules can be coupled to a particular remote device. For example, one module can be coupled to a remote device. In another example, two or more modules (each having any number of sensors) are coupled to a remote device.

The remote device can be a multi-function device, such as a handheld organizer (personal digital/data assistant), cellular telephone, netbook computer, laptop computer, desktop computer, or other device.

The sensors can include oximetry sensor and the module can be described as oximetry hardware. In various examples, the module includes any combination of analog circuitry, digital circuitry, software, and firmware. For example, a module can include an amplifier, such as a pre-amplifier or a power amplifier. The module can provide an output to the remote device that is encoded in an analog signal, a digital signal (having binary states), or a discrete signal (having any number of discrete states).

The module can have various components configured to perform a variety of functions. In one example, the module includes an analog circuit such as an amplifier or an analog processor. In one example, the module includes a digital circuit (including logic gates) or a digital processor. In one example, the module includes an analog-to-digital converter (ADC), a digital-to-analog converter (DAC), or a multiplexor/demultiplexor.

In addition, the module can provide an output independent of the remote device. For example, the module can include one or more optical elements or light elements that are operated based on a measured parameter. In one example, a display screen of the module provides an optical indication of the measured parameter. In one example, the module provides an audible or tactile output to indicate a measured parameter or a fault condition.

In one example, the module provides oximetry data (or oximetry information) to a remote device.

The module can be configured to identify a sensor to which it is coupled. The sensor can, for example, include a particular configuration of emitters and detectors (and be tailored for use on a particular tissue). As such, the module can determine the type of sensor and provide the appropriate timing information and communication services to support that type of sensor. In one example, the module includes a user-operable input (such as a keypad or touch-sensitive screen) and the user is prompted to enter sensor identification information. The sensor identification information is stored in a memory of the module and is used to calibrate the output signal provided to the remote device.

In one example, the module has no external control elements and is configured to operate autonomously when put into service (as detected by a sensor signal, for example). In one example, the module includes user-operable switches or other input devices to allow a user to configure the module for a particular monitoring function. In one example, the module includes a plurality of switches to allow user selection of calibration data or to enable a user to tailor module parameters for a particular measurement function. The sensor can provide its own individual calibration data to the module through a communication channel.

In one example, the module is powered by a battery or other portable power source. In one example, the module is powered by an electrical coupling with the remote device or an electrical coupling with a powered sensor. The module can include a recharging circuit to service an internal battery power supply.

Various functions can be performed by the module. For example, a module can include components configured to provide partially, or wholly, processed data to a remote device. In the case of wholly processed data, the remote device functions as a dumb terminal and, in one example, provides a visible display. In the case of partially processed data, the remote device is tailored to complete the processing and provide display or other services.

In one example, the module includes a housing in which selected components are affixed. In one example, the module is fabricated in a portion of an electrical wire conductor and is protected by an overmolded portion. In one example, the module is fabricated as part of a fan-out cable or fabricated as a separate housing.

One example includes an oximeter system having any number of oximeters (or sensors) sending measurements to a remote device (such as a display monitor). The module provides a timing signal or a control signal to the sensors. The timing signal or control signal is used by the sensor to control the operation of one or more light emitters. The sensor also is configured to generate a signal corresponding to a measured parameter. The measured parameter can include optical data, thermal data, pressure data or other such physical parameter. In one example, the sensor generates optical data using a photodetector. The module can be configured to perform some or all of signal analysis and provide an output that is either partially or fully processed. The output is provided to a remote device which, in one example, includes a display monitor.

In addition, the module can be configured to signal an alarm condition. The alarm condition may denote an equipment failure or a measurement excursion beyond a prescribed window. In one example, an alarm condition is communicated to the remote device for display.

In one example, the module can be coupled to a plurality of sensors. The sensors can be synchronized in time to reduce the likelihood of one sensor interfering with a light signal of another sensor.

The module can be configured to provide oxygen saturation measurements from tissue. In addition, the module can be configured to provide a measure of pulse oximetry or a measure of regional oximetry. Pulse oximetry provides a measure of oxygen saturation of blood, and according to one example, is derived from a ratio of light absorption of pulsating components. As such, pulse oximetry reflects oxygenation of arterial blood using an alternating current (AC) component of a measurement signal. Regional oximetry, sometimes referred to as tissue oximetry, is derived from a direct current (DC) component of a measurement signal and reflects oxygenation of a region, or tissue, at the measurement site. A DC signal is unmodulated and non-pulsatile and, in the context of the present subject matter, corresponds to a physiological parameter of the tissue. Regional oximetry can be measured using near infrared spectroscopy.

In one example, the module is configured to self-synchronize the sensors. As such, the remote device provides no control signal to the module and the control, measurement, and analysis occurs within one or more modules. The remote device serves as a display monitor.

A sensor, according to one example, is configured to encode selected calibration data. Calibration data can be encode as stored data in an on-board memory of the sensor, as a value of an electrical component (such as a resistance value), or as a mechanical feature that is recognized by a corresponding connector (in a wired communication channel example). The calibration data can include site-specific data that denotes a particular site for placement of the sensor. A site can be an ear lobe, a finger, a forehead, or other tissue site. The calibration data can include application-specific data. An application can refer to cerebral oximetry that represents tissue oxygenation for a brain. In addition, an application can include pulse oximetry suitable for use on a finger or toe. The calibration data can also include data specific to a particular sensor. An example includes data denoting a wavelength for an emitter, sensitivity information for a detector, or other variable that may arise during the manufacture of a sensor.

A module can be configured to store data from a sensor or store processed data. The processed data can include oximetry data, temperature data, pulse data, or other measured parameter. The module can be configured to store the data and, upon a triggering event, send the data to the remote device. The triggering event can include detection of an operable communication channel, establishment of an electrical connection, passage of a particular time, comparison of a measured parameter with a stored value, state of charge of a battery, or other event.

In one example, a module provides multiple data streams to the remote device. The multiple data streams include a fast stream that provides near real-time measurement of oximetry data suitable for archival purposes or for later analysis. In addition, the multiple data streams include a slow stream suitable for display on a monitor. The slow stream data changes value more slowly and corresponds to a time-wise smoothing of the data.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device comprising:
   a first sensor coupler configured to receive a first input signal from a first sensor, the first input signal corresponding to a non-pulsatile direct current (DC) component of a first physiological parameter and based on optical excitation of a tissue;
   a processor coupled to the first sensor coupler, the processor configured to generate an output signal based on the first input signal, the first physiological parameter encoded in the output signal and the output signal differing from the first input signal, and wherein the output signal corresponds to a measure of tissue oxygenation; and
   an output coupler configured to communicate the output signal to a remote device.

2. The device of claim 1 wherein the first sensor coupler includes at least one of an electrical connector and an optical connector.

3. The device of claim 1 wherein at least one of the first sensor coupler and the output coupler includes at least one of a wireless receiver or a wireless transmitter.

4. The device of claim 1 further including a second sensor coupler configured to receive a second input signal from a second sensor, the second input signal corresponding to a second physiological parameter and wherein the processor is coupled to the second sensor coupler, the output signal based on the second input signal.

5. The device of claim 1 further including a user-operable switch coupled to the processor.

6. The device of claim 1 wherein the processor is configured to generate a timing signal.

7. The device of claim 1 wherein the processor includes at least one of an amplifier, an analog-to-digital converter, a digital-to-analog converter, a multiplexer, and a filter.

8. The device of claim 1 wherein the output coupler includes at least one of an electrical connector and a wireless transmitter.

9. The device of claim 1 wherein the output signal is encoded with a calculated value configured for rendering on a visual display.

10. A method comprising:
    exchanging a first timing signal with a first sensor, the first sensor configured to provide a detected signal corresponding to an optical property of a tissue correlated with the first timing signal;
    receiving the detected signal;
    processing the detected signal to generate an output signal, the output signal corresponding to a parameter of the tissue, the parameter based on a non-pulsatile direct current (DC) component of the detected signal, and the output signal different than the detected signal, the parameter corresponding to a measure of tissue oxygenation; and
    communicating the output signal to a remote device.

11. The method of claim 10 wherein exchanging the first timing signal includes at least one of sending or receiving relative to the first sensor.

12. The method of claim 10 further including exchanging a second timing signal relative to a second remote sensor based on the exchanging of the first timing signal.

13. The method of claim 10 wherein receiving the detected signal includes receiving wirelessly.

14. The method of claim 10 wherein processing the detected signal includes at least one of amplifying, converting to digital, converting to analog, multiplexing, and filtering.

15. The method of claim 10 wherein communicating includes transmitting wirelessly.

16. A system comprising:
    at least one sensor having a detector and configured to provide a sensor signal corresponding to an optical property of tissue;
    a processor coupled to receive the sensor signal and configured to generate an output signal using the sensor signal, the output signal corresponding to a non-pulsatile direct current (DC) component of a parameter of the tissue, the output signal different than the sensor signal, the parameter corresponding to a measure of tissue oxygenation; and
    a monitor coupled to receive the output signal and configured to render a user perceivable representation of the parameter.

17. The system of claim 16 wherein the at least one sensor includes at least one of a plurality of emitters and a plurality of detectors.

18. The system of claim 16 wherein the at least one sensor is coupled to the processor by a wireless link.

19. The system of claim 18 wherein the wireless link includes at least one of a fiber optic element and a radio frequency transmitter.

20. The system of claim 16 wherein the processor includes at least one of an analog processor, a digital processor, a filter, a converter, and an amplifier.

21. The system of claim 16 wherein the monitor includes at least one of a visual display and a printer.

\* \* \* \* \*